United States Patent

Isaji et al.

[11] Patent Number: 6,114,383
[45] Date of Patent: Sep. 5, 2000

[54] DRUGS INHIBITING PROGRESS OF PTERYGIUM AND POSTOPERATIVE RECURRENCE OF THE SAME

[75] Inventors: Masayuki Isaji; Hiroshi Miyata; Yukiyoshi Ajisawa, all of Nagano, Japan

[73] Assignee: Kissei Pharmaceutical Co., Ltd., Japan

[21] Appl. No.: 09/355,342

[22] PCT Filed: Feb. 13, 1998

[86] PCT No.: PCT/JP98/00582

§ 371 Date: Aug. 6, 1999

§ 102(e) Date: Aug. 6, 1999

[87] PCT Pub. No.: WO98/35668

PCT Pub. Date: Aug. 20, 1998

[30] Foreign Application Priority Data

Feb. 14, 1997 [JP] Japan .................................. 9-68882

[51] Int. Cl.⁷ .................................................. A61K 31/24
[52] U.S. Cl. ............................................................ 514/535
[58] Field of Search .............................................. 514/535

[56] References Cited

U.S. PATENT DOCUMENTS 5,288,503  2/1994  Wood et al. .............................. 424/497
5,356,620  10/1994  Yamamoto et al. ................... 424/78.04
5,385,935  1/1995  Tamai et al. ............................. 514/535

*Primary Examiner*—Raymond Henley, III
*Attorney, Agent, or Firm*—Liniak, Berenato, Longacre & White

[57] ABSTRACT

The present invention relates to an agent inhibiting progress of pterygium and postoperative recurrence of the same. N-(3,4-Dimethoxycinnamoyl)anthranilic acid represented by the formula:

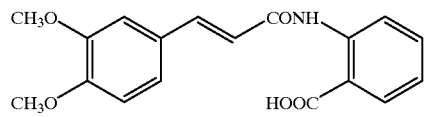

or a pharmaceutically acceptable salt thereof has an inhibitory activity on proliferation of pterygium tissues, and a pharmaceutical composition comprising as the active ingredient the same is useful as an agent inhibiting progress of pterygium and postoperative recurrence of the same.

9 Claims, 1 Drawing Sheet

Tranilast Concentrations ($\mu g/ml$)

DRUGS INHIBITING PROGRESS OF PTERYGIUM AND POSTOPERATIVE RECURRENCE OF THE SAME

This is a 371 of PCT/JP98/00582 filed Feb. 13, 1998.

TECHNICAL FIELD

The present invention relates to a pharmaceutical composition which is useful as an agent for inhibiting progress of pterygium and postoperative recurrence of the same.

More particularly, the present invention relates to an agent for inhibiting progress of pterygium and postoperative recurrence of the same, which agent comprises as the active ingredient N-(3,4-dimethoxycinnamoyl)anthranilic acid (generic name: tranilast) represented by the formula:

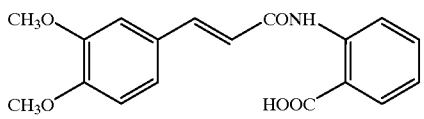

or a pharmaceutically acceptable salt thereof.

BACKGROUND ART

Pterygium is an ocular disease which is characterized by the encroachment of a fleshly and congestively triangular portion of the bulbar conjunctiva onto the cornea and caused by external stimuli such as ultraviolet light, dry atmosphere, heat, cold and dust. In particular, pterygium has been largely observed on the cornea at the nasal side along the palpebral fissure. Pterygium progresses gradually toward the top of the cornea from the conjunctiva and reaches the pupillary area to cause visual loss. At the present time, there is no therapeutic agent which can inhibit or which is effective against the progress of pterygium. Therefore, development of an effective therapeutic agent against this disease has been desired. Accordingly, pterygium treatment, has involved only surgical operations such as to remove pterygium tissues.

Unfortunately pterygium surgery, there is a high incidence of recurrence of pterygium, about 30–50%, which remains a serious problem. Therefore, in the field of the pterygium medication, earnest studies have been actively promoted in order to find substances which are effective for inhibiting the recurrence of pterygium. Up to this time, for example, it was confirmed that anti-tumor agents such as mitomycin were effective. However, concern regarding theses drugs have been raised relative to the incidence of serious side effects such as scleromalacia [Connective Tissue, Vol.26, pp135–137 (1994) etc.]. In view of said concerns, such drugs have not been sufficiently tested enough to use clinically. In addition, it has been reported that beta-ray radiation using strontium 90 was effective in inhibiting postoperative recurrence of pterygium. However, injuries such as cataract formation have been noted [Ganka, Vol.24, pp917–923 (1982) etc.].

On the other hand, tranilast has been widely used as a drug for the treatment of allergic disorders such as bronchial asthma, allergic rhinitis, atopic dermatitis and allergic conjunctivitis, and cutaneous disorders such as keloid and hypertrophic scaring. For example, it has been known that tranilast has inhibitory activities on chemical mediator release caused by an allergic reaction, excessive collagen accumulation by fibroblast cells in cutaneous tissues and excessive proliferation of smooth muscle cells in coronary artery vessels.

However, it has not been disclosed that tranilast has an inhibitory activity on progress of pterygium and postoperative recurrence of the same and it is not known that tranilast is useful as an agent for inhibiting the progress of pterygium and postoperative recurrence of the same.

SUMMARY OF THE INVENTION

The present invention relates to an agent for inhibiting the progress of pterygium and postoperative recurrence of the same, which comprises as the active ingredient N-(3,4-dimethoxycinnamoyl)anthranilic acid represented by the formula:

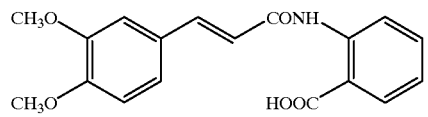

or a pharmaceutically acceptable salt thereof.

The present inventors have earnestly studied to find compounds which have an inhibitory activity on the proliferation of pterygium tissues. As a result, it was found that tranilast has a marked inhibitory effect on proliferation of pterygium tissues and is extremely useful as an agent for inhibiting the progress of pterygium and postoperative recurrence of the same, thereby forming the basis of the present invention.

DETAILED DESCRIPTION OF THE INVENTION

Figure 1:
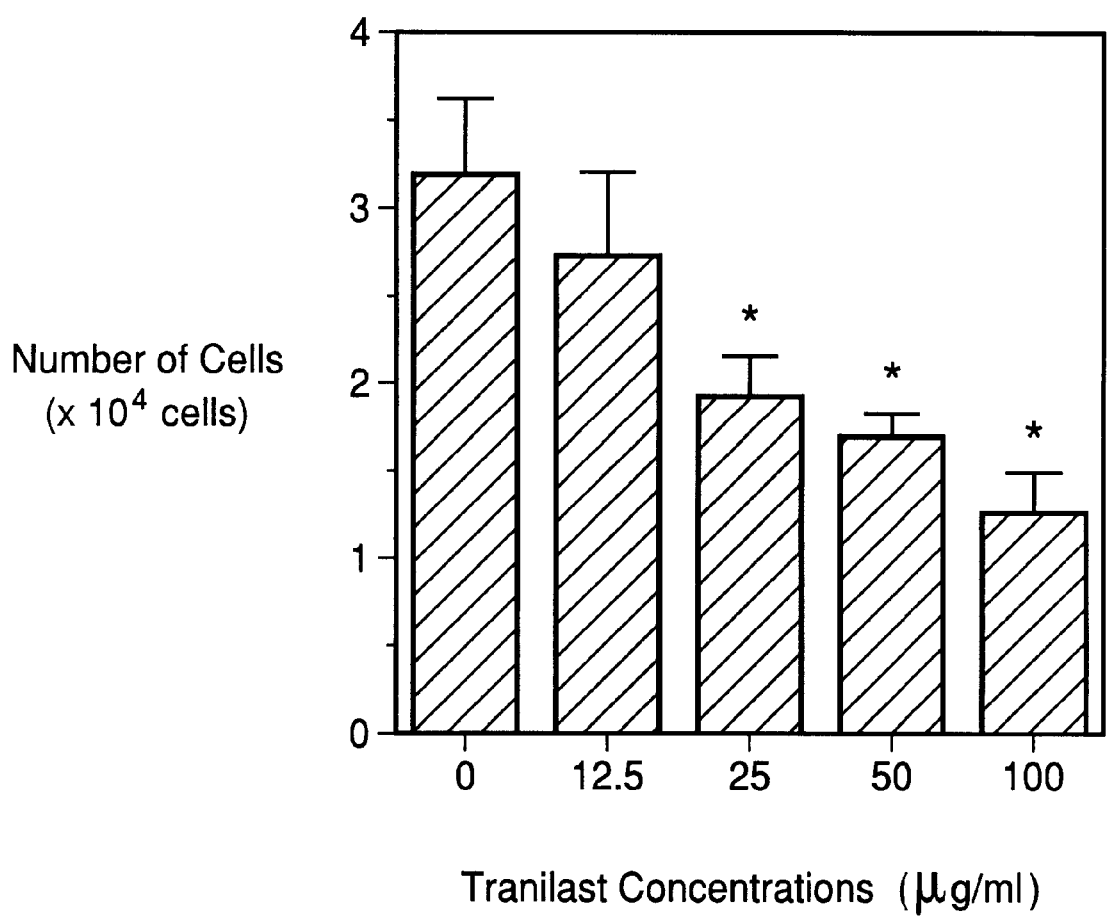
FIG. 1 is a graph illustrating the inhibitory activity on proliferation of human pterygium tissue-derived cells by tranilast. The ordinal axis shows number of human pterygium tissue-derived cells (x 104 cells), and the axis of the abscissas shows tranilast concentrations ($\mu$g/ml). The symbol * in the graph indicates significant differences at $p<0.01$.

The present inventors have confirmed that tranilast significantly suppressed proliferation of pterygium tissues in the in vitro test for inhibition of cell proliferation using pterygium tissue-derived cells.

As a consequence, tranilast has been found to have a highly significant inhibitory effect on the proliferation of pterygium tissue-derived cells and is an extremely useful compound as an agent for inhibiting the progress of pterygium and postoperative recurrence of the same.

Pharmaceutical compositions which are useful as agents inhibiting the progress of pterygium and postoperative recurrence of the same in accordance with this invention can be prepared comprising as the active ingredient tranilast or a pharmaceutically acceptable salt thereof.

Various methods for the preparation of tranilast and salts thereof which are active ingredients are known, and these compounds can be readily prepared according to methods described in the literature and the like (Japanese Patent Application Publication (kokoku) No.Sho.56-40710; ibid. No.Sho.57-36905; ibid. No.Sho. 58-17186; ibid. No.Sho.58-48545; ibid. No.Sho.58-55138; ibid. No.Sho.58-55139; ibid. No.Hei.01-28013; ibid. No.Hei.01-50219; ibid. No.Hei.03-37539 etc.).

As examples of pharmaceutically acceptable salts of tranilast, salts with inorganic bases such as a sodium salt and a potassium salt, salts formed with organic amines such as morpholine, piperazine, piperidine and pyrrolidine and salts formed with amino acids can be illustrated.

The pharmaceutical compositions of the present invention can be employed in the practical treatment, of inhibiting the progress of pterygium by being administered orally, or preferably, topically as eyedrops, eye ointments and the like.

For example, eyedrops can be formulated by dissolving tranilast or a pharmaceutically acceptable salt thereof together with a basic substance with heating in a proper quantity of sterilized water in which a surface active agent is dissolved, adding polyvinylpyrrolidone, and optionally adding appropriate pharmaceutical additives such as a preservative, a stabilizing agent, a buffer, an isotonicity, an antioxidant and a viscosity improver to dissolve completely.

Eye ointments can be appropriately formulated by using bases which are generally used in eye ointments. Eye ointments can be also used as reversible thermally gelling water-base pharmaceutical compositions.

When the pharmaceutical compositions of the present invention are employed in practical treatment, the dosage of tranilast or a pharmaceutically acceptable salt thereof as the active ingredient is appropriately decided depending on the age, degree of symptoms of each patient to be treated, therapeutic value and the like. The dosage should be fixed at an appropriate concentration to be curable. For example, in case of eyedrops, preferably a 0.001–2 weight % concentration of tramlast can be used. Eyedrops are applied 1 to several times per day and applied at a dose of 1 to several droplets per time.

Best Mode for Carrying Out the Invention

The present invention is further illustrated in more detail by way of the following Example.

EXAMPLE

Inhibitory activity on proliferation of pterygium tissue-derived cells

① Culture of Pterygium Tissue-derived Cells

Human pterygium tissues were cut into narrow strips. The strips were adhered to a culture plate and subcultured in Dulbecco's modified Eagle's Medium (DMEM) containing 10% fetal calf serum (FBS) at 37° C. in an atmosphere of 5% $CO_2$ in air. At the point that cells were migrated and proliferated from the tissues, the medium was aspirated and cells were washed with phosphate-buffered saline (PBS(−)) gently. Then, the PBS(−) was aspirated, an aliquot of 0.25% trypsin solution containing 0.02% EDTA was added to the culture plate, and the morphology of cells was observed under phase-contrast microscopy. When cells were going to be round, an equal value of DMEM containing 10% FBS was added to the trypsin solution to stop the action of trypsin. Attached cells were harvested from the plate by pipetting the medium using a slender pasteur pipette. The cell suspension was transferred into spit, then medium was added to the spit, and the cell suspension was mixed about 20 times vigorously by pipetting with a pasteur pipette and centrifuged at 100–110 xg for 1 minute. After the supernatant was discarded, fresh medium was added to the precipitate, and the pterygium-derived cell suspension was prepared by pipetting using a pasteur pipette. The suspension was further subcultured in DMEM containing 10% FBS to use for the experiment.

② Preparation of Test Drugs

Tranilast was added to a 1% aqueous sodium bicarbonate solution at a final concentration of 1.0% and dissolved by warming at 70° C. The solution was sterilized with a millipore filter and diluted with DMEM containing 10% FBS to a final prescribed concentration.

③ Experimental Method

DMEM medium (2 ml) containing cells ($2 \times 10^4$ cells) and 10% FBS was added to each well using a culture plate (6-well), and cultured. After 1 day, the medium was aspirated, DMEM medium (2 ml) containing various concentrations of tranilast and 10% FBS was added to the plate, and cultured at 37° C. in an atmosphere of 5% $CO_2$ in air. After 2 days, the medium was aspirated, the cells were washed with PBS(−), and 1 ml of 0.25% trypsin solution containing 0.02% EDTA was added to the plate. After harvesting cells from the plate by pipetting using a pasteur pipette, the number of viable cells was counted under phase-contrast microscopy using a hemocytometer.

④ Assessment of Effect

Mean and standard error values of each group were calculated. Statistical analysis of significance was performed by a one-way analysis of variance and statistical significance was confirmed. Thereafter, analysis of the significance between groups was performed by Dunnett's multiple test.

⑤ Results

As shown in FIG. 1, tranilast significantly suppressed the proliferation of pterygium tissue-derived cells in a concentration-dependent manner.

Industrial Applicability

A pharmaceutical composition of the present invention comprising as the active ingredient tranilast has a marked inhibitory activity on proliferation of pterygium tissues and is suitable as an agent inhibiting progress of pterygium and postoperative recurrence of the same.

What is claimed is:

1. A method for prevention or treatment of pterygium or postoperative recurrence of the same in a human patient, which comprises administering to the patient N-(3,4-dimethoxycinnamoyl)anthranilic acid represented by the formula:

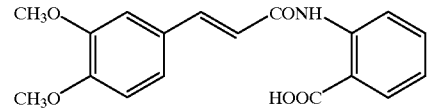

or a pharmaceutically acceptable salt thereof.

2. The method of claim 1, wherein said N-(3,4-dimethoxycinnamoyl)anthranilic acid is administered to a patient having symptoms of pterygium.

3. The method of claim 1, wherein N-(3,4-dimethoxycinnamoyl)anthranilic acid is administered to a patient who has had a surgical operation to remove pterygium tissues.

4. The method of claim 1, wherein said N-(3,4-dimethoxycinnamoyl)anthranilic acid is administered orally.

5. The method of claim 2, wherein said N-(3,4-dimethoxycinnamoyl)anthranilic acid is administered orally.

6. The method of claim 3, wherein said N-(3,4-dimethoxycinnamoyl)anthranilic acid is administered orally.

7. The method of claim 1, wherein said N-(3,4-dimethoxycinnamoyl)anthranilic acid is administered topically as an eyedrop or eye ointment.

8. The method of claim 2, wherein said N-(3,4-dimethoxycinnamoyl)anthranilic acid is administered topically as an eyedrop or eye ointment.

9. The method of claim 3, wherein said N-(3,4-dimethoxycinnamoyl)anthranilic acid is administered topically as an eyedrop or eye ointment.

* * * * *